United States Patent [19]

Neesby

[11] Patent Number: 4,735,967

[45] Date of Patent: * Apr. 5, 1988

[54] METHOD FOR DESENSITIZING THE GASTROINTESTINAL TRACT FROM FOOD ALLERGIES

[76] Inventor: Torben E. Neesby, 2842 E. Griffith, Fresno, Calif. 93726

[*] Notice: The portion of the term of this patent subsequent to Jan. 26, 2005 has been disclaimed.

[21] Appl. No.: 763,035

[22] Filed: Aug. 5, 1985

Related U.S. Application Data

[63] Continuation-in-part of Ser. No. 738,883, May 28, 1985, which is a continuation of Ser. No. 638,061, Aug. 6, 1984, abandoned.

[51] Int. Cl.$^4$ .............................................. A61K 31/255
[52] U.S. Cl. ...................................... 514/557; 514/558
[58] Field of Search ................................... 514/557, 558

[56] References Cited

U.S. PATENT DOCUMENTS

| | | | |
|---|---|---|---|
| 3,088,866 | 5/1963 | Wernicoff et al. | 424/234 |
| 3,326,754 | 6/1967 | Prussin et al. | 424/244 |
| 3,564,098 | 2/1971 | Erwin et al. | 514/557 |
| 3,708,578 | 1/1973 | Das | 424/141 |
| 3,849,558 | 11/1974 | Nakamura et al. | 424/234 |
| 3,995,056 | 11/1976 | Allais et al. | 424/317 |
| 4,123,382 | 10/1978 | Morse et al. | 252/316 |

OTHER PUBLICATIONS

Kirk–Othmer—2nd Ed., vol. 3, pp. 881, (1966).

*Primary Examiner*—Leonard Schenkman
*Attorney, Agent, or Firm*—Lyon & Lyon

[57] ABSTRACT

There is disclosed a method for treatment of human food allergies by desensitizing the gastrointestinal tract comprising the oral ingestion of an effective dosage of a chemical composition of short chain fatty acids of molecular composition having from 4 to 12 carbon atoms per molecule in a neutralized state.

28 Claims, No Drawings

METHOD FOR DESENSITIZING THE GASTROINTESTINAL TRACT FROM FOOD ALLERGIES

RELATED APPLICATIONS

This is a continuation-in-part of U.S. Ser. No. 738,883, filed May 28, 1985 which is a continuation in U.S. Ser. No. 638,061, filed Aug. 6, 1984, now abandoned, all of the same title.

BACKGROUND OF THE INVENTION

1. Field of the Invention

The field of the present invention relates generally to a method for treatment of human food allergies and sensitivities in a human host having human food allergies and sensitivities by desensitizing the gastrointestinal tract and through this treatment, improved nutritional status and glandular and mental functions.

2. Description of the Prior Art

Food allergies and sensitivities are an important cause of illness in both children and adults. Allergies, including food allergies, remain the leading chronic diseases in patients under seventeen years old. Symptoms commonly known to accompany food allergies include headaches, stomach aches, depression, wheezing, fatigue, irritability, hyperactivity, skin rashes, drowsiness, and circles under the eyes. The incidence of allergy-related nutritional deficiencies is also significant due to the necessary avoidance of the offending foods.

Traditional treatment methods include injections and sublingual dropletss of dilute extracts of the allergens which may cause anaphylactic shock. Food allergy sufferers mav also be instructed to avoid a particular food, often disguised in the prepared foods so prevalent today. These treatments presuppose identification of the offending food.

Identification of food allergens is often elusive due to the time lag between ingestion and the onset of symptoms. Clinical identification methods, including trial elimination diets and food skin tests, are lengthy, costly and often inconclusive.

The present invention relieves sufferers from food allergies and its symptoms without the need to identify the particular allergen thereby avoiding the problematic identification procedures and expense as well as uncertainty associated therewith.

SUMMARY OF THE INVENTION

In the present invention, a method for the oral administration of a composition comprised of effective amounts of at least one alkali salt of a short chain fatty acid having from 4 to 12 carbon atoms per molecule is provided to alleviate and finally eliminate food allergies by desensitizing the gastrointestinal tract. The short chain fatty acid may be neutralized by a non-toxic alkali metal such as lithium, sodium, potassium, calcium, magnesium, zinc, or rubidium. The short chain fatty acid is preferably a butyrate or a butyrate and a combination of capric, caprylic and/or caproic acid. The B vitamins, particularly $B_2$ vitamin riboflavin, may be added to compensate for resultant B vitamin deficiency which may be associated with oral administration of butyric acid and/or salts thereof. A time-release preparation of cellulose acetate phthalate, wax or other accepted agents may also be added to the granulated or finely-powdered butyrates to prevent stomach irritation.

The advantages of the present invention include:

(1) effectiveness without regard to problematic and expensive identification of the offending food;

(2) no risk of anaphylactic shock present as with conventional diagnosis and treatment of food allergies since its constituents are considered foods and no restrictions are limiting their use in nutrition;

(3) concurrent benefits such as greater emotional stability and feeling of well-being; and (4) ability of complement with the recognized anti-anxiety remedies such as tranquilizers or other medications such as antifungal agents.

Accordingly, it is an object of the present invention to provide a method of treatment of food allergies in a human host having human food allergies and sensitivities by desensitizing the gastrointestinal tract. Other objects and advantages will be apparent to those skilled in the art in connection with the detailed description and examples set forth below.

DESCRIPTION OF THE PREFERRED EMBODIMENT

In its preferred embodiment, the method comprises the oral administration of an effective dosage of a composition of at least one alkali salt of butyric acid. Butyric acid is operable per se in this invention. The salts of butyric acid are, however, preferred to the acid per se or its esters because they have less offensive odor and flavor. Such salts are comprised of alkali metals which include lithium, sodium, potassium, calcium, magnesium, rubidium or zinc. The magnesium and calcium salts are particularly preferred to those of sodium or potassium salts because the cations of these salts are only partially absorbed by the gastrointestinal tract and this eases the load on the kidneys, a load which is caused by the alkalosis created when butyric acid metabolizes into $CO_2$ and is expelled through the lungs leaving the alkaline cations to be excreted through the kidneys. ("Butyrate" hereinafter refers to butyric acid or a salt thereof.)

In the practice of the present invention, it is preferred that the mixture further comprise $B_2$ vitamin riboflavin in the amount of at least about 25 mg. up to about 100 mg. per 500 mg. of short chain fatty acid to compensate for riboflavin deficiency, which may be caused by increased metabolism of short chain fatty acids.

It is also preferred that the mixture further comprise an enteric coating material for time release delaying action to alleviate possible stomach irritation caused by butyrate intake. Suitable time release material for the practice of the present invention includes cellulose acetate phthalate or a non-toxic wax with a melting point over about 40° C. A preferred suitable oral dosage composition may comprise from about 35 to about 65 percent by weight of a time-release material such as cellulose acetate phthalate or a non-toxic wax with a melting point over about 40° C. However, it will be obvious to one skilled in the art that other types of time releasing preparations may also be utilized in connection with the practice of the present invention. By way of example only, U.S. Pat. No. 3,849,558, the disclosure of which is incorporated herein by reference, makes known a composition and method wherein pharmaceutical compositions with controlled rates of gastrointestinal absorption are prepared by dissolution or suspension of the therapeutically active agent in an absorption depressive agent.

To prepare a composition utilizing a wax material for time release action, by way of example only, 1 kg of a wax marketed under the trademark Glycol Wax is melted by heating up to 150° C. Next, between about 0.8 to about 1.7 kg of calcium and magnesium salts of a short chain fatty acid having from 4 to 12 carbon atoms per molecule is added and the mixture is stirred to get a dough-like consistency. After the material has cooled and turned brittle, the material can be ground up and then measured into capsules.

In a preferred embodiment, a coated butyrate with or without riboflavin may also be used in combination with individual or combinations of effective amounts of sodium salts of capric acid, caproic acid, and caprylic acid as long as the mixtures contain at least about 40% butyrate. In this case, the alkali salt of butyric acid is ⅔ calcium butyrate and ⅓ magnesium butyrate and approximately ⅓ of the butyric acid is neutralized by magnesium. This oral dosage composition is comprised of from about 0.7% to about 13% B vitamin riboflavin.

In accordance with the method of this invention, butyrate is administered orally which may, for example, be in either tablet or capsule form. The normal dosage required is in an amount of one to two grams of butyrate for each dose to be administered. However, of course, this dosage may vary depending upon the age and weight of the subject. A dose should preferably be taken at each meal for a total daily intake of about 0.5 to about 10 grams butyrate although the dosage could be as high as 30–40 grams per day. Desensitization is seen in about 1 to 2 weeks whereas improvements in glandular functions have been observed after longer administration time.

The following examples will aid in explaining the preparation of the various salts of the present invention but are intended to be illustrative only, and not limiting:

EXAMPLE 1

40 g. of sodium hydroxide were dissolved in 100 ml. of water and cooled to 30° C. 88 g. of butyric acid were stirred slowly into the sodium hydroxide solution. The pH of the solution was adjusted to 7.2 by addition of either sodium hydroxide or butyric acid. The sodium butyrate was then cooled, cut into small pieces, and dried. The dried sodium butyrate was ground to a granulate condition and the mixture was filled into a size 00 gelatin capsule accommodating 500 to 600 mg. sodium butyrate.

EXAMPLE 2

40 g. of magnesium oxide and 82 g. of calcium hydroxide were added to 400 ml. water. While stirring the mixture, 370 g. of butyric acid were added. The salts were maintained at a high temperature and continually stirred until they had attained a smooth condition. The pH was adjusted to 7.4. The mixture was cooled and spread on a glass tray which was placed in a drying oven until the mixture became dry and then was ground and granulated.

EXAMPLE 3

56 g. of potassium hydroxide were dissolved in 70 ml. water and the solution was cooled to about 20° C. 88 g. of butyric acid were added slowly with stirring. Potassium butyrate was vacuum dried and then ground finely and granulated.

EXAMPLE 4

One gram mole of sodium hydroxide was dissolved in 100 ml water. The equivalent weight of caproic acid was added to the solution. The mixture was then dried and added to butyrate as prepared in Examples 1, 2, and 3.

EXAMPLE 5

Example 4 was repeated except that caprylic acid was substituted for caproic acid.

EXAMPLE 6

Example 4 was repeated except that capric acid was substituted for caproic acid. A mixture was then made comprising, by way of example only, 50% butyrate, 5% caproate, 20% caprylate, and 20% caprate.

EXAMPLE 7

An alcoholic solution of ethyl cellulose was then added to the dried finely powdered mixture of butyrate as prepared in Examples 1 through 6 in sufficient amounts to give a final granulation containing from about 15% to about 30% of ethyl cellulose.

EXAMPLE 8

50 g. of $B_2$ vitamin riboflavin was added to 1,000 g. of dried granulated butyrate as prepared in Examples 1 through 6.

The toxicity of butyrates starts only a concentrations of 20-30 millimole and depends upon the kind of cells exposed to the butyrates. Butyrate esters are present in milk and butterfat. Thus, for example, one quart of milk contains approximately one gram of butyric acid as a triglyceride ester while butterfat contains around 3%. Butyric acid is one of the so-called short chain fatty acids (SCFA) and it is only synthesized in the mammary glands. Because of its offensive odor, butyric acid is therefore only usable as a neutral salt when it is applied as an intestinal desensitizer.

Butyrates are catabolized the usual way in the cells and can be infused intravenously in amounts of 20-30 gm/day in which case it is catabolized rapidly by the hepatic mitochondria.

In vitro experiments with additions of butyrates to cultures of various cells show butyrates exhibit a low toxicity beginning with some inhibition at 5-10 millimole concentration, depending upon the kind of cells. The inhibition of normal growth is reversible meaning that growth takes place when the butyrate is removed from the culture.

In clinical studies of a composition administered according to the present invention, butyrates have shown the surprising effect of removing intestinal sensitivity to various foods when it has been taken regularly for a few days. Some patients have experienced rapid relief, while in other patients the freedom from adverse effects of otherwise offending food(s) have taken up to a week to become obvious.

Butyrates apparently have no side effects when taken as a supplemental nutrient and are classified by the Department of Agriculture as a food.

The kinds of patients who appear to benefit most are described in the following two detailed case histories. Various chemical, biochemical and hematological tests have been performed on the patients. The tests show that no deleterious effects take place and many parameters improve during the administration of butyrates.

The beneficial effect of the butyrate may start at a dose level of only one capsule/day (about 500–600 mg of SCFA) but many patients may require from 3 to 5 capsules (at 550 mg of SCFA) per meal in order to feel comfortable.

Although the other members of the SCFAs also seem to have a beneficial effect upon the gastrointestinal tract, the presence of the butyrate appears to enhance the beneficial effects of the other members. Thus, for a more broad effect, a combined salt of butyric and caprylic acids may be preferable.

When a subject is receiving a dosage of between about 500 to about 1200 mg of SCFAs at a time, special precautions to prevent alkalosis usually are not necessary. However, when a subject is taking more than 1200 mg of SCFAs in a single dosage, then the problem of alkalosis may arise. Thus, for example, if the dosage is taken after each meal, the buffering effect of the SCFAs may increase the pH of the stomach content to between about 3 to about 5, to thereby counteract the normal action of hydrochloric acid secreted by the parietal glands to thereby give rise to uncontrolled intestinal fermentation. In addition, such a dosage may cause the urine to be alkaline and thereby encourage bacterial growth. In order to prevent alkalosis, an acid may be ingested to counteract the effect of the SCFAs. Thus, where more than about 1200 mg SCFAs are taken at a given time, it is advisable to take the SCFAs at least two hours after a meal or one hour before the meal. However, in all cases, the SCFAs should be taken together with a glass or two of water or fruit juice.

Further, the biochemical/physiological effects of the short-chain fatty acids are such that a slight inhibition of the oxidative phosphorylation in the mitochondria will start at concentrations of 0.5 moles. See, Harker, *Effect of Octanoate on Rat Brain and Liver Mytochondria*, Neurology, 1983 33 1374–9, the disclosure of which is specifically incorporated herein by reference. See also, Zieve, et al, *Toxicity of Fatty Acids and Ammonia Interaction with Hypoglycemia and Krebs Cycle Inhibition*, Journal of Lab and Clinical Medicine, 1983 101, p. 930–7, the disclosure of which is also specifically incorporated herein by reference. Thus, it is of importance to dilute and distribute the SCFAs, and one of the ways to do this is to make the SCFAs into a time-release preparation. This approach, as compared to offsetting the alkaline nature of the SCFAs by an acid, has been preferred by patients over prolonged periods of time.

In its preferred dosage, a composition according to the present invention will be administered three times a day, for at least a week, to deliver between about 0.5 to about 10 grams of SCFA/day. This dosage, of course, will vary depending upon the individual subject.

The symptoms which have been chosen as an indication for treatment with butyrates and other SCFAs are those connected with gastrointestinal sensitivity to various foods.

The primary effects of such sensitivities are often in the realm of vasomotor malfunctions which may affect both the digestive organs as well as any other organ of the human body.

The etiology, development and biochemistry are presently not known in detail although a number of theories have been proposed.

Presumably, both the integrity of the brush border cell lining of the small intestines as well as the capacity of the Peyer's patches to produce various lymphocytes are the pivotal points in the development of sensitivity towards foods and other orally ingested allergens. Finally, the functions of the colonic cells appear very important too.

The gastrointestinal sensitivity can be both a fast onset of pain in the stomach area and the upper quadrant—but it can also be a slowly developing uneasiness, diffuse pressure, swelling and pain in the lower quadrant as well as hyperacidity and so-called heart burn. Quite often, the gastrointestinal distress might be overlooked because the patient may take "neutralizers" for the excess stomach acid.

The secondary appearance of vasomotor malfunction could be edema, rashes, itchings and pains in various organs. It is most noticeable when these troubles occur in the skin, the sinuses, the joints or in the central nervous system.

The investigations on the effects of butyrates and other SCFAs upon this complex malfunction have been done on ambulatory patients, mostly so-called "free-living"—meaning non-hospitalized persons—who were otherwise healthy. Their blood chemistries were within normal ranges except for serum triglycerides which tended to be elevated. The CBC (complete blood count) were likewise normal except for a 2 mg lower hemoglobin (RBC) and often an elevated eosinophil count indicating an allergic response.

More detailed analysis of B & T cells tended likewise to show slightly or even severely depressed T cell counts ($<60\%$) and depressed suppressor T cells ($<20\%$).

The gastro-enterologists tended to call this disturbance "irritable bowel syndrome" and experimentally treated the patients with a drug marketed under the trademark "TRIAVIL" which made the patients very relaxed for four to six weeks after which the symptoms generally had disappeared. In many cases, the symptoms would slowly come back.

Many GI doctors preferred to treat their patients with a drug marketed under the trademark "TAGAMET"—a very potent synthetic antihistamine which is especially effective in protecting the stomach from the excessive histamine released from the mast cells and the neutrophiles during the allergic reaction. Quite often, this release (by degranulation) will last for many hours as the antigenic food component is being absorbed from the GI tract.

Both TRIAVIL and TAGAMET as well as other tranquilizers and antihistamines can cause severe side effects which may limit their desirability.

The protocol followed in clinical evaluation of the method and compositions of the present invention did not provide double blind controlled studies. It must, however, be considered that these patients mostly had long case histories which were recorded in the files of the medical doctor(s). Therefore, they all had long periods which served as "controls" showing the ineffectiveness of the common remedies with which they had been treated prior to the treatment with butyrates and/or other short chain fatty acids.

The patients were accepted into this protocol after reviewing the case history and, if necessary, were given a physical and/or CBC, and blood and urine chemistries. Their complaints of sensitivities and allergic responses were reviewed.

Generally, the patients were given a bottle of calcium and magnesium salts of butyric or other short chain fatty acids and were instructed to take one capsule (about 550 mg of SCFA) after breakfast for three consecutive days. If no improvement had taken place (or no adverse effects), the dose was increased to one capsule twice a day for the next three days and, pending the response, to one capsule three times a day. Other increases could be made if necessary to obtain relief from the sensitivities. Quite a number of patients obtained relief by taking one capsule at breakfast and, if necessary, taking another one at suppertime. Many other patients had to take up to four capsules at every meal in order to feel comfortable. Some patients would take the capsules every day, while others would take them for two weeks and then stop for some weeks.

The reason for the slow increase in dosage which has been recommended is the biochemical effect of butyric acid and other short chain fatty acids. If a capsule contains 550 mg butyrate, this corresponds to approximately 4 millimoles butyrate if the stomach content is 1000 milliliters. Mostly, the stomach content would be around 600 ml., depending upon the size of the meal. Thus, one capsule could contribute 4–7 millimole of butyric acid in the GI tract. This is a concentration which might cause some reaction, such as a slight feeling of uneasiness or presssure, although by no means a dangerous reaction.

By starting slowly, the GI tract would acquire resistance to the short chain fatty acids and a patient would have no untoward reaction when taking four or five capsules after a meal. It should be noted that these acids are naturally occurring food components and the concentrations of the free acids in the acid stomach content can reach levels of millimoles, for example, after eating 1 oz. Roquefort or blue cheese. The acids are absorbed rapidly into the blood and catabolized by the mitochondrial enzymes in a few hours. However, while an effective dosage may be as low as 0.5 grams SCFA per day, clinical studies tend to indicate that a more uniform effective dosage may begin at 3 grams SCFA per day. Further, it is usually necessary that the treatment be continued for at least one week.

The effects of the short chain fatty acids upon the brush border cells, the colonic mucosal cells and the immune system have been investigated by in vitro investigations and reported in the scientific literature. This is, however, the first time that it has been reported that these acids have clinical effects as assessed by both objective and subjective means.

After a regular administration of butyrate at the level of three to four capsules (each capsule having about 550 mg of SCFA)/meal for one month, the immune system appeared to be improved as deemed by the % T cells and the % suppressor T cells. In more than 80% of the patients, a high degree of freedom of untoward reactions to food was acquired.

DETAILED CASE HISTORY

I. The subject was a female, age 19, first seen in a clinic on Sept. 4, 1982. The subject weighed 103 pounds, had a blood pressure of 100/60 and a pulse of 90. The subject was given a RAST test on Sept. 15, 1982, with the following results:

| Grasses | | Weeds | |
|---|---|---|---|
| 0 $G_2$ bermuda grass | 411 | 0 $W_2$ ragweed | 247 |
| 0 $G_5$ perennial rye | 254 | 0 $W_6$ Calif. sage | 417 |
| 0 $G_6$ timothy | 193 | 0 $W_9$ English plantain | 332 |
| 0 $G_{10}$ johnson | 352 | 0 $W_{11}$ Russian thistle | 342 |
| | | 0 $W_{15}$ scale | 352 |
| | | 0 $W_{18}$ sheep sorrel | 307 |

-continued

| | | | |
|---|---|---|---|
| | | 0 $W_{10}$ lambs qtr | 287 |
| | | 0 $W_{14}$ pigweed | 500 |
| Epidermals | | Molds | |
| 0 $E_1$ cat | 313 | 0 $M_1$ penicillium | 314 |
| 0 $E_2$ dog | 363 | 0 $M_2$ cladosporium | 277 |
| | | 0 $M_3$ aspergillus | 245 |
| Foods | | 0 $M_6$ altemaria | 371 |
| 0 $F_2$ milk | 425 | | |
| 0 $F_4$ wheat | 423 | Dust | |
| | | 0 $H_2$ house dust | 304 |
| Trees | | 0 $D_2$ dust mite | 111 |
| 0 $T_1$ maple | 324 | | |
| 0 $T_2$ alder | 296 | | |
| 0 $T_7$ oak | 284 | | |
| 0 $T_8$ elm | 419 | | |
| 0 $T_9$ olive | 296 | | |
| 0 $T_{10}$ walnut | 280 | | |
| 0 $T_{11}$ sycamore | 312 | | |
| 0 $T_{14}$ cottonwood | 358 | | |
| 0 $T_{16}$ pine | 309 | | |
| 0 $T_{12}$ willow | 363 | | |

There was no elevated IgE for inhalant allergies, including cat and dog dander. Molds, milk, wheat and dust were also low. A pap smear was negative. The treatment prescribed was antihistamines.

On Mar. 28, 1983, the subject came in for more rast tests which were performed on Apr. 1, 1983 and Apr. 15, 1983. These results are set forth below:

| Foods | | Epidermals | |
|---|---|---|---|
| 0 $F_1$ egg | 550 | 1 $E_1$ cat | 960 |
| 1 $F_2$ milk | 824 | 2 $E_2$ dog | 1650 |
| 0 $F_4$ wheat | 499 | | |
| 0 $F_8$ corn | 646 | Trees | |
| 1 $F_{13}$ peanut | 1027 | 1 $T_1$ maple | 1510 |
| 0 $F_{14}$ soybean | 697 | 1 $T_2$ alder | 1200 |
| 1 $F_{25}$ tomato | 864 | 1 $T_7$ oak | 904 |
| 1 $F_{26}$ pork | 768 | 1 $T_8$ elm | 1220 |
| 1 $F_9$ rice | 1088 | 1 $T_9$ olive | 1080 |
| 0 $F_{35}$ potato | 526 | 1 $T_{10}$ eucalyptus | 908 |
| 1 F yeast | 766 | 1 $T_{11}$ sycamore | 1130 |
| | | 1 $T_{14}$ cottonwood | 1190 |
| Grasses | | 1 $T_{16}$ pine | 1230 |
| 1–2 $G_2$ bermuda grass | 1591 | 1 $T_{12}$ willow | 850 |
| 1–2 $G_5$ perennial rye | 1550 | | |
| 1 $G_6$ timothy | 1490 | Molds | |
| 1–2 $G_{10}$ johnson | 1540 | 1–2 $M_1$ penicillium | 1580 |
| | | 1 $M_2$ cladosporium | 920 |
| Weeds | | 2 $M_3$ aspergillus | 1670 |
| 1 $W_2$ ragweed | 918 | — $M_5$ candida | 780 |
| 1 $W_6$ Calif. sage | 1100 | 2 $M_6$ altemaria | 1755 |
| 2 $W_9$ English plantain | 1800 | | |
| 1 $W_{11}$ Russian thistle | 1100 | Dust | |
| 1 $W_{14}$ pigweed | 1002 | 1 $H_2$ house dust | 1458 |
| 1 $W_{18}$ sheep sorrel | 790 | 1–2 $D_2$ dust mite | 1520 |
| 1 $W_{10}$ lambs qtr | 1260 | | |

Thus, when compared with the test done in September of 1982, a general elevation was observed for both inhalant allergies as well as foods. The subject now had a weight of 107 pounds with a blood pressure of 100/60. The subject complained of being dizzy after eating (usually ten minutes after eating). The subject ate a lot of cheese but did not drink milk. The subject was given shots of allergen extracts for treatment.

On Aug. 16, 1983, the subject again complained that she was still having allergic responses and was treated with antihistamine.

On Mar. 25, 1985, the subject again complained that the allergies continued. Other symptoms included nasal congestion and pressure, nose itches, clear nasal mucous, nasal membranes edmatous and pale, a clear discharge post nasal drip and her nose was getting worse. The subject also complained of food intolerances. Cola and candy made her sick to her stomach and a glucose tolerance test was normal, indicating no diabetic tendencies. There was no glucosuria. The subject was given two capsules per meal of an oral dosage composition having about 550 mg. of butyrate.

The followup with the subject indicated that she was experiencing relief from her allergy symptoms and was continuing to follow the treatment.

DETAILED CASE HISTORY

The subject was female, age 44. The subject was first seen on Oct. 29, 1984, and weighed 139½ pounds with a blood pressure of 132/80 and a pulse of 98. At that time, she complained of a possible candida infection. The subject complained that four months ago, a burning sensation in urethra had been treated by a doctor for bladder problem. The subject took KEFLEX TM for dental work and had been hooked on codeine and DEMEROL TM due to severe pain in epigastric area. Her tongue was very coated with a white layer and she was given NIZEROL TM for systematic candidiasis. She was also given NYSTATIN TM and a MYCOLOG TM ointment.

The subject was seen again on Nov. 9, 1984, at which time she indicated some improvement but still had complaints. Her weight was 144 pounds, her blood pressure was 106/70 and her pulse was 88.

The subject was seen again on Nov. 20, 1984, at which time she weighted 140 pounds, had a blood pressure of 104/70 and a pulse of 100. Once again, there was some improvement, but she still had complaints, including a headache.

On Nov. 27, 1984, the subject was seen again and weighed 141 pounds, had a blood pressure of 110/88 and a pulse of 90. The subject complained about food allergies and a sore throat.

On Dec. 19, 1984, the subject underwent RAST tests and had the following results:

| Grasses (4) | | Weeds (7) | |
|---|---|---|---|
| 0 | $G_2$ bermuda grass | 0 | $W_2$ ragweed |
| 0 | $G_5$ perennial rye | 0 | $W_6$ Calif. sage |
| 0 | $G_6$ timothy | 0 | $W_9$ English plantain |
| 0 | $G_{10}$ johnson | 0 | $W_{11}$ Russian thistle |
| | | 0 | $W_{15}$ scale |
| | | 0 | $W_{18}$ sheep sorrel |
| | | 0 | $W_{10}$ lambs qtr |
| Epidermals (2) | | 0 | $W_{14}$ pigweed |
| 0 | $E_1$ cat | Foods (14) | |
| 0 | $E_2$ dog | | $F_1$ egg 605 |
| | | 0 | $F_2$ milk 361 |
| Trees (10) | | | $F_3$ codfish 167 |
| 0 | $T_1$ maple | 0 | $F_4$ wheat 503 |
| 0 | $T_2$ alder | | $F_7$ oats 323 |
| 0 | $T_7$ oak | | $F_8$ corn 553 |
| 0 | $T_8$ elm | | $F_{13}$ peanut 303 |
| 0 | $T_9$ olive | | $F_{14}$ soybean 528 |
| 0 | $T_{10}$ walnut | | $F_{25}$ pork 339 |
| 0 | $T_{11}$ sycamore | | $F_{33}$ orange 332 |
| 0 | $T_{14}$ cottonwood | | $F_9$ rice 287 |
| 0 | $T_{16}$ pine | | $F_{15}$ beans 231 |
| 0 | $T_{12}$ willow | | $F_{35}$ potato 320 |
| | | | F chocolate 338 |
| Molds | | | F beef 384 |
| 0 | $M_1$ penicillium 284 | | |
| 0 | $M_2$ cladosporium 247 | | |
| 0 | $M_3$ aspergillus 246 | | |
| | $M_5$ candida 219 | | |

| -continued | | |
|---|---|---|
| 0 | $M_6$ altemaria | 203 |
| Dust (2) | | |
| 0 | $H_2$ house dust | 276 |
| 0 | $D_2$ dust mite | 2783 |

The RAST test results were low except for dust and mites and the subject was given shots.

On Jan. 9, 1985, the subject was seen again. A Nickerson smear was negative and vaginal itching was worse since the night before. The subject had a red area by her urether and had cold extremities. The subject was given niacin 50 mg t.i.d. and was increased to 100-150 mg. MYCOLOG TM cream was also prescribed for the subject.

On Feb. 26, 1985, the subject weighed 135 pounds, had a blood pressure of 100/70 and a pulse of 76. The subject was taking NYSTATIN TM, Niacin and PREMARIN TM 0.625 mg.

On Apr. 15, 1985, the subject weighed 132 pounds, had a blood pressure of 108/67 and a pulse of 88. The subject complained of vaginal itching for 7-10 days. There was no discharge. The subject complained it was painful to move her eyes and was more sensitive to light although there was no photophobia and no visible floating. The subject was bothered by severe neck tenseness in muscles. Analogy indicated that the cranial nerve was intact. The subject was given a refill of DARVACET TM.

On Apr. 18, 1985, the subject was given MONISTAT TM.

On May 14, 1985, the subject had severe headaches and was given TRANXENE TM.

On May 20, 1985, the subject still complained of severe headaches, nausea and tension headaches.

On May 22, 1985, the subject had a vaginal yeast infection.

On May 28, 1985, the subject felt like the candida was back in the vagina. The subject had been under stress and had vaginal white discharges.

On May 29, 1985, the subject had tension headaches and itching all over her body.

On June 4, 1985, the subject complained she felt as if her head was full and she thought she had an infection in sinus.

On June 7, 1985, the subject had more complaints and was started on one to two capsules, three times a day, of an oral dosage composition having about 550 mg. of butyrate.

On June 14, 1985, the subject complained that pollen was bothering her. Her neck and headache had been better for a week.

On July 3, 1985, the subject complained of a vaginal discharge with bad odor, some headache. The subject was also given a prescription for DARVOCET TM and FLAGYL TM.

On July 8, 1985, the subject weighed 119 pounds, had a blood pressure of 100/68 and a pulse of 90. The subject indicated that her symptoms had improved.

On about July 15, 1985, the subject indicated that her symptoms were still improved and the subject was started on a dosage of two tablets, three times a day of an oral dosage composition in unit dosage form of a solid having approximately 370 mg. of butyrate, 120 mg. of caprylate (a neutral caprylic acid) and 350 mg. of non-toxic wax having a melting point greater than about 40° C.

The following are abbreviated case histories of the treatment with calcium magnesium butyrate of persons with food intolerances. The proportion of calcium to magnesium is 2:1. It is to be understood that these histories are given by way of illustration and not of limitation.

CASE HISTORY NO. I

Male, age 71. The subject took a dosage of 3–4 unit doses having about 550 mg of butyrate 3 times a day. Improvement was seen within a week and in three months, the subject was markedly relieved of his food sensitivity. The 2:1 mixture of calcium-magnesium butyrate was administered in combination with the antifungal drug, MYSTATIN TM.

CASE HISTORY NO. II

Female, age 68, with a long history of food sensitivities. The subject took a dosage of 3 tablets having about 550 mg. of butyrate 3 times a day. The subject was markedly relieved from symptoms after treatment for three months.

CASE HISTORY NO. III

Female with a long history of disabling migraine headaches was initially started on one capsukle per day containing about 550 mg. of butyrate. The dosage was subsequently increased to one capsule twice a day. The subject was practically free of headaches after two months of treatment.

CASE HISTORY NO. IV

Young male had multiple food sensitivities, especially to wheat products. He took 3 tablets, three times a day, each tablet having about 550 mg butyrate. After several days, he stopped having wheat sensitivity. After several months of treatment, the subject discontinued the treatment and the wheat sensitivity eventually returned. When treatment was resumed, the subject took 2 tablets, three times a day, each tablet having about 300 mg caprylic acid. The treatment gave relief from the sensitivity and the subject switched to 3 tablets, three times a day, each tablet having approximately 370 mg of butyrate, 120 mg of caprylate and 350 mg of non-toxic wax having a melting point greater than about 40° C.

CASE HISTORY NO. V

Male, age 21, with multiple food sensitivities. The subject had been receiving allergy shots for 37 allergy components for a couple of years but still suffered from food sensitivities. The subject began taking 2–3 tablets, 3 times a day, each tablet having about 550 mg butyrate. The symptoms of food sensitivities went away and the subject was able to decrease the frequency of the allergy shots.

CASE HISTORY NO. VI

Female with multiple food allergies had been receiving allergy shots for a couple of years but still suffered from food sensitivities. When the subject began taking 2–3 tablets, 3 times a day, each tablet having about 550 mg. butyrate, the symptoms of food sensitivities went away and the subject was able to decrease the frequency of the allergy shots.

CASE HISTORY NO. VII

Male with wheat and cheese sensitivity. The subject took 3 tablets, 3 times a day, each tablet having about 550 mg. butyrate. After about six months, the subject stopped taking the butyrate and did not have any symptoms of food sensitivity.

CASE HISTORY NO. VIII

Female, age 28, with wheat sensitivity causing an arthritic-like condition. The subject had been getting homeopathic treatment and in combination with the calcium-magnesium butyrate, the subject was markedly relieved of her food sensitivity.

Having fully described the present invention, it will be apparent from the above description that various modifications may be made within the scope of the invention. Therefore, the invention is not intended to be limited except as may be required by the lawful scope of the following claims.

What is claimed is:

1. A method for treating human food allergies and sensitivities in a human host having human food allergies and sensitivities comprising the daily oral administration of an effective dosage of one or more compositions of a non-toxic alkali salt of a short chain fatty acid of molecular composition having from 4 to 12 carbon atoms per molecule.

2. A method as recited in claim 1 comprising the further step of oral administration of an acidic agent other than the alkali salt of the short chain fatty acid of claim 1 to prevent alkalosis.

3. A method as recited in claim 1 wherein the non-toxic alkali salt of a short chain fatty acid is comprised of an alkali metal selected from the group consisting of: sodium, potassium, calcium, magnesium, zinc, lithium and rubidium.

4. A method as recited in claim 1 wherein the effective dosage is at between about 0.5 to about 10 grams of an alkali salt of a short chain fatty acid per day.

5. A method as recited in claim 1 wherein the dosage is taken with each meal.

6. A method as recited in claim 1 wherein the dosage is taken three times a day.

7. A method as recited in claim 1 wherein the alkali salt of a short chain fatty acid is comprised of a butyrate.

8. A method as recited in claim 7 wherein the alkali salt of butyric acid is comprised of ⅔ calcium butyrate and ⅓ magnesium butyrate.

9. A method as recited in claim 1 wherein the composition further comprises B vitamins.

10. A method as recited in claim 1 wherein the composition is comprised of about 25 mg. up to about 100 mg. riboflavin per 500 mg. of an alkali salt of a short chain fatty acid.

11. A method as recited in claim 10 wherein the effective dosage of one or more compositions is comprised of a mixture containing at least about 40% by weight of a butyrate and a sodium salt of capric acid, caproic acid or caprylic acid.

12. A method as recited in claim 1 wherein the composition further comprises a time-released preparation.

13. A method as recited in claim 12 wherein said preparation contains cellulose acetate phthalate.

14. A method as recited in claim 1 wherein the composition is administered at least three times a day for at least one week.

15. A method as recited in claim 1 wherein the composition additionally comprises sodium caprate, sodium caprylate, or sodium caproate.

16. A method of treating a human subject afflicted with food allergies or sensitivities which method comprises:

administering to the subject a daily dosage composition containing an amount of a non-toxic alkali salt of a short chain fatty acid of molecular composition having 4, 6, 8, or 10 carbon atoms per molecule effective for the treatment of food allergies or sensitivities in about 35 to about 65 percent by weight based on the total weight of the composition of time release material, and repeating the dosage until the subject no longer exhibits symptoms of the food allergies or sensitivities.

17. A method as recited in claim 16 wherein the alkali salt of a short chain fatty acid is comprised of a butyrate.

18. A method as recited in claim 16 wherein the time release material is a non-toxic wax having a melting point greater than about 40° C.

19. An oral dosage composition in unit dosage form comprising from about 35 to about 65 percent by weight based on the total weight of the composition of a time released material and from about 14% to about 65% by weight of a non-toxic salt of a short chain fatty acid of molecular composition having from 4 to 12 carbon atoms per molecule.

20. An oral dosage composition as recited in claim 19 further comprising from about 1% to about 39% of an alakli salt of short chain fatty acid having from 5 to 12 carbon atoms per molecule.

21. An oral dosage composition as recited in claim 20 wherein the short chain fatty acid is selected from the group consisting of caproic, caprylic and capric acid.

22. An oral dosage composition as recited in claim 19 wherein the non-toxic salt is comprised of an alkali salt of butyric acid, said alkali salt comprising at least one non-toxic alkali metal selected from the group consisting of: sodium, potassium, calcium, magnesium, zinc, lithium and rubidium.

23. An oral dosage composition as recited in claim 22 wherein the alkali salt of butyric acid is comprised of ⅔ calcium butyrate and ⅓ magnesium butyrate.

24. An oral dosage composition as recited in claim 19 further comprising from about 0.7% to about 13% of the B vitamin riboflavin.

25. An oral dosage composition as recited in claim 19 wherein the time release material is a non-toxic wax having a melting point greater than about 40° C.

26. An oral dosage composition as recited in claim 19 further comprising an acidic agent other than the non-toxic salt of claim 19 to prevent alkalosis.

27. An oral dosage composition as recited in claim 19 further comprising about 25 mg. up to about 100 mg. riboflavin per 500 mg. of an alkali salt of a short chain fatty acid.

28. An oral dosage composition as recited in claim 19 wherein the non-toxic salt is comprised of a mixture containing at least about 40% by weight of a butyrate and a sodium salt of capric acid, caproic acid or caprylic acid.

* * * * *